US006174320B1

(12) United States Patent
Kugel et al.

(10) Patent No.: US 6,174,320 B1
(45) Date of Patent: *Jan. 16, 2001

(54) HERNIA MESH PATCH WITH SLIT

(75) Inventors: Robert D. Kugel, Olympia, WA (US); J. Douglas Inman, Arlington; Keith D. Biggers, Southlake, both of TX (US)

(73) Assignee: Bard Asdi Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/365,379

(22) Filed: Aug. 2, 1999

Related U.S. Application Data

(63) Continuation-in-part of application No. 09/304,365, filed on May 4, 1999, which is a continuation of application No. 09/006,653, filed on Jan. 14, 1998, now Pat. No. 5,916,225, which is a continuation of application No. 08/755,108, filed on Nov. 22, 1996, now Pat. No. 4,769,864, which is a continuation-in-part of application No. 08/315,249, filed on Sep. 29, 1994, now Pat. No. 5,634,931.
(60) Provisional application No. 60/095,586, filed on Aug. 6, 1998.

(51) Int. Cl.[7] .................................................... A61B 17/04
(52) U.S. Cl. ............................................................ 606/151
(58) Field of Search ................................ 606/1, 110–114, 606/127, 213, 151, 200; 623/11; 602/58

(56) References Cited

U.S. PATENT DOCUMENTS

| 2,671,444 | 3/1954 | Pease, Jr. ............................... 606/151 |
| 3,054,406 | 9/1962 | Usher ...................................... 606/151 |
| 4,007,743 | 2/1977 | Blake . |
| 4,347,847 | 9/1982 | Usher ...................................... 606/151 |

(List continued on next page.)

FOREIGN PATENT DOCUMENTS

| 2114282 | 7/1994 | (CA) . |
| 0 362 113 | 4/1990 | (EP) . |
| 0 474 887 | 10/1991 | (EP) . |
| 676 285 | 7/1979 | (SU) . |
| 782 814 | 11/1980 | (SU) . |
| WO 90/14796 | 12/1990 | (WO) . |
| WO 93/17635 | 9/1993 | (WO) . |
| WO 96/09795 | 4/1996 | (WO) . |
| wo 97/22310 | 6/1997 | (WO) . |

OTHER PUBLICATIONS

Gregory L. Brown, M.D. et al., "Comparison of Prosthetic Materials for Abdominal Wall Reconstruction in the Presence of Contamination and Infection", Annals of Surgery, Jun. 1985.) vol. 201, pp. 705–711.

Scott D. Jenkins, M.D. et al., "A Comparison of Prosthetic Materials Used to Repair Abdominal Wall Defects", Surgery, Aug. 1983, vol. 94, No. 2, pp. 392–398.

"Prevention of Postsurgical Adhesions by Interceed (TC7)", Fertility and Sterility, Jun. 1989, vol. 51, No. 6, pp. 933–938.

Hernando Cordona M.D., "Prosthokeratoplasty", 1983, Cornea, vol. 2, No. 3, 1983, pp. 179–183.

Alonzo P. Walker, M.D., et al., "Double–Layer Prostheses for Repair of Abdominal Wall Defects in a Rabbit Model", pp. 32–37, Journal of Surgical Research, vol. 55, No. No. 1, Jul. 1993.

*Primary Examiner*—Gary Jackson
(74) *Attorney, Agent, or Firm*—Wolf, Greenfield & Sacks, P.C.

(57) ABSTRACT

A hernia patch having a first layer of inert synthetic mesh material. A second layer of a inert synthetic mesh material overlies the first to create a pouch between the first and second layers. A curved elongated resilient member adjacent a periphery of the pouch for creating tension in both layers and a slit in the layers of mesh material extending inward from an outer edge and terminating in an enlarged opening for placement around a patient's chord structure.

12 Claims, 2 Drawing Sheets

U.S. PATENT DOCUMENTS

| | | | |
|---|---|---|---|
| 4,452,245 | 6/1984 | Usher | 606/151 |
| 4,561,434 | 12/1985 | Taylor | 606/151 |
| 4,633,873 | 1/1987 | Dumican et al. | 606/151 |
| 4,655,221 | 4/1987 | Devereux | 606/151 |
| 4,693,720 | 9/1987 | Scharnberg et al. | 623/11 |
| 4,710,192 | 12/1987 | Liotta et al. | 623/1 |
| 4,769,038 | 9/1988 | Bendavid | 623/13 |
| 4,796,603 | 1/1989 | Dahlke | 128/899 |
| 4,854,316 | 8/1989 | Davis . | |
| 4,865,026 | 9/1989 | Barrett . | |
| 4,955,907 | 9/1990 | Ledergerber | 623/8 |
| 5,006,106 | 4/1991 | Angelchik | 600/37 |
| 5,059,205 | 10/1991 | El-Nounou et al. . | |
| 5,116,357 | 5/1992 | Eberbach | 606/151 |
| 5,122,155 | 6/1992 | Eberbach | 606/151 |
| 5,141,515 | 8/1992 | Eberbach | 606/151 |
| 5,147,374 | 9/1992 | Fernandez | 606/151 |
| 5,147,384 | 9/1992 | La Rocca . | |
| 5,147,387 | 9/1992 | Jansen | 623/1 |
| 5,176,692 | 1/1993 | Wilk et al. | 606/151 |
| 5,192,301 | 3/1993 | Kamiya et al. | 606/213 |
| 5,195,542 | 3/1993 | Gazielly et al. | 602/44 |
| 5,201,745 | 4/1993 | Tayot et al. | 606/151 |
| 5,254,133 | 10/1993 | Seid . | |
| 5,258,000 | 11/1993 | Gianturco . | |
| 5,290,217 | 3/1994 | Campos . | |
| 5,334,217 | 8/1994 | Das | 606/213 |
| 5,350,399 | 9/1974 | Erlebacher et al. | 606/213 |
| 5,356,432 | 10/1994 | Rutkow et al. . | |
| 5,366,460 | 11/1994 | Eberbach | 606/151 |
| 5,368,602 | 11/1994 | de la Torre | 606/151 |
| 5,370,650 | 12/1994 | Tovey et al. . | |
| 5,397,331 | 3/1995 | Himpens et al. | 606/151 |
| 5,425,744 | 6/1995 | Fagan et al. | 606/213 |
| 5,433,996 | 7/1995 | Kranzler et al. | 428/247 |
| 5,451,235 | 9/1995 | Lock et al. | 623/12 |
| 5,456,720 | 10/1995 | Schultz et al. | 623/11 |
| 5,507,811 | 4/1996 | Koike et al. | 623/11 |
| 5,593,441 | 1/1997 | Lichtenstein et al. | 623/11 |
| 5,614,284 | 3/1997 | Kranzler et al. | 428/138 |
| 5,634,931 | 6/1997 | Kugel | 606/151 |
| 5,695,525 | 12/1997 | Mulhauser et al. | 623/11 |
| 5,702,416 | 12/1997 | Kieturakis et al. | 606/193 |
| 5,716,408 | 2/1998 | Eldridge et al. | 623/11 |
| 5,743,917 | 4/1998 | Saxon | 623/11 |
| 5,766,246 | 6/1998 | Mulhauser et al. | 623/11 |
| 5,769,864 | 6/1998 | Kugel | 606/151 |
| 5,824,082 | 10/1998 | Brown | 623/11 |
| 5,836,961 | 11/1998 | Kieturakis et al. | 606/190 |
| 5,879,366 | 3/1999 | Shaw et al. | 606/213 |
| 5,916,225 | 6/1999 | Kugel | 606/151 |
| 5,919,232 | 7/1999 | Chaffringeon et al. | 623/11 |
| 5,922,026 | 7/1999 | Chin | 623/11 |
| 5,954,767 | 9/1999 | Pajotin et al | 623/11- |

HERNIA MESH PATCH WITH SLIT

CROSS-REFERENCE TO RELATED APPLICATION

This application claims the benefit of provisional application Ser. No. 60/095,586, filed Aug. 6, 1998, and is a continuation-in-part of application Ser. No. 09/304,365, filed May 4, 1999 which was a continuation of application No. 09/006,653, filed Jan. 14, 1998, Pat. No. 5,916,225, which is a continuation of application No. 08/755,108, Nov. 22, 1996, Pat. No. 5,769,864, which is a continuation-in-part of application No. 08/315,249, Sep. 29, 1994, Pat. No. 5,634,931.

TECHNICAL FIELD

The present invention generally relates to a surgically implantable patch for use in repairing a hernia of other wound. More particularly, the present invention relates to a hernia repair patch having a slit for receiving a patient's chord structure when placing a patch in a patient for hernia repair.

BACKGROUND

Surgically implantable mesh patches for the repair of inguinal and other abdominal wall hernias, which are intended for permanent placement within a patient's body space, have been provided and used previously. Tension free surgical repairs of hernias have been developed using synthetic mesh materials to bridge and to patch hernia defects. These repairs resulted in both a decrease in the recurrence rate as well as a decrease in the amount of a patient's post operative discomfort. Patients undergoing these more advanced procedures were able and are able to resume their normal activities sooner.

Some of these earlier techniques are somewhat complicated. Several use a plug or a locating member to fit within the hernia defect itself. Also, many of these earlier techniques were designed specifically for use in laparoscopic repair of hernias. Moreover, many of the prior inventions required suturing to the patient's body tissue. Although these medical advances are acknowledged for their usefulness and success, there remains a need or needs for more improvements in the surgical repair of hernias. In particular, a need exists for an improved implantable patch having a slit for receiving a patient's chord structure to facilitate a Lichtenstein repair.

DISCLOSURE OF INVENTION

A hernia mesh patch for use in the surgical repair of a patient's inguinal or other abdominal wall hernias, or other tissue apertures, is disclosed for permanent placement within a patient's body space. The hernia mesh patch of the invention has a top and a bottom layer of an inert, synthetic mesh, preferably polypropylene mesh, secured to each other with a seam. The seam has an opening for allowing a slit to pass from an edge of the patch to an opening in the interior of the patch.

To serve a spring function, an implantable inert monofilament fiber, arranged in a partial oval, ovoid, loop having a circumference slightly greater than the circumference of the interior pocket volume of this patch, is inserted into this pocket to keep the hernia mesh patch expanded under tension in a planar configuration. A border on at least one of the layers extends outward past the seam. The border preferably has slits to fill uneven voids in the patient's tissue and fit more tightly. The monofilament fiber has ends that terminate at the slit. An access opening is provided at the center of a layer so that a surgeon can insert his finger into an interior pouch to manipulate the patch more effectively.

Without the need for general anesthesia, nor expensive laparoscopic instrumentation, a surgeon, when repairing an inguinal hernia, makes a small incision in the patient, approximately four to six centimeters-long, arranged obliquely, over the area of the internal ring location of the inguinal hernia. The external oblique fascia is opened through the external ring of the inguinal hernia.

Thereafter, the surgeon manually lays the patch under the level of the external oblique fascia and over the internal oblique muscle in the patient's inguinal canal space. The cord structures that extend to the testicle are allowed to pass through the slit in the patch which otherwise covers the hernia defect in the patient's abdominal wall. The incision is then closed with stitches.

Soon after surgery, the patient's body reacts to the mesh of the hernia mesh patch, and in a short time, the mesh becomes stuck, thereby keeping the hernia mesh patch in place. Thereafter, the patient's scar tissue grows into the mesh over a period of time, between thirty and sixty days, to permanently fix the hernia mesh patch in its intended position over the repaired area, where the hernia was located.

Preferably, small holes are cut through both layers of the mesh inside the fiber ring to increase friction and to minimize sliding or migration of the hernia mesh patch after it is positioned.

BEST MODE FOR CARRYING OUT THE INVENTION

Figure 1:
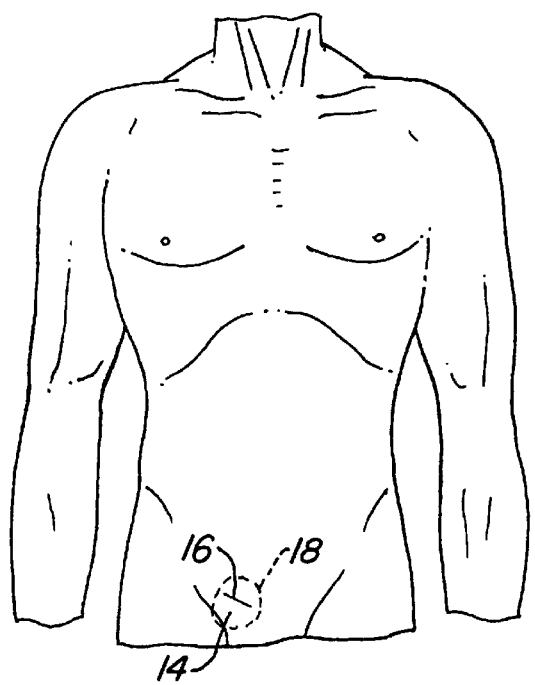
FIG. 1 is a schematic partial front view of a patient's body.

The hernia mesh patch 10, illustrated in the drawings, is surgically permanently implantable within a patient's body space to adequately cover, correct, prevent and repair any inguinal or other abdominal wall hernias, other types of hernias or tissue apertures. The surgeon has the objective of making a sutureless repair, by first cutting an approximately four to six centimeter incision 16 that is obliquely positioned approximately over the location described as the internal ring 18, where an inguinal hernia 14 has occurred, as shown in FIG. 1. The surgeon then works through the incision 16 and inserts the hernia mesh patch 10, using a technique to effect a Lichtenstein repair.

Figure 2:
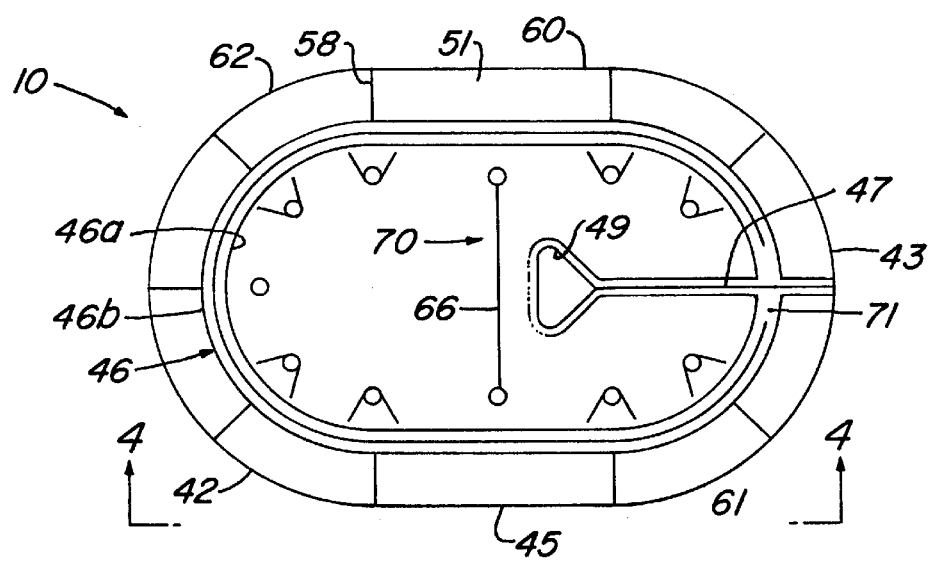
FIG. 2 is a top view of a preferred embodiment of the surgically implantable hernia repair mesh patch.
Figure 4:
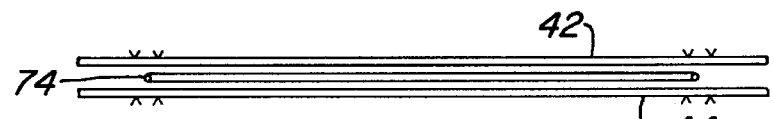
FIG. 4 is a sectional exploded view of the patch of FIG. 2, taken along the line 4—4 of FIG. 2.
Figure 3:
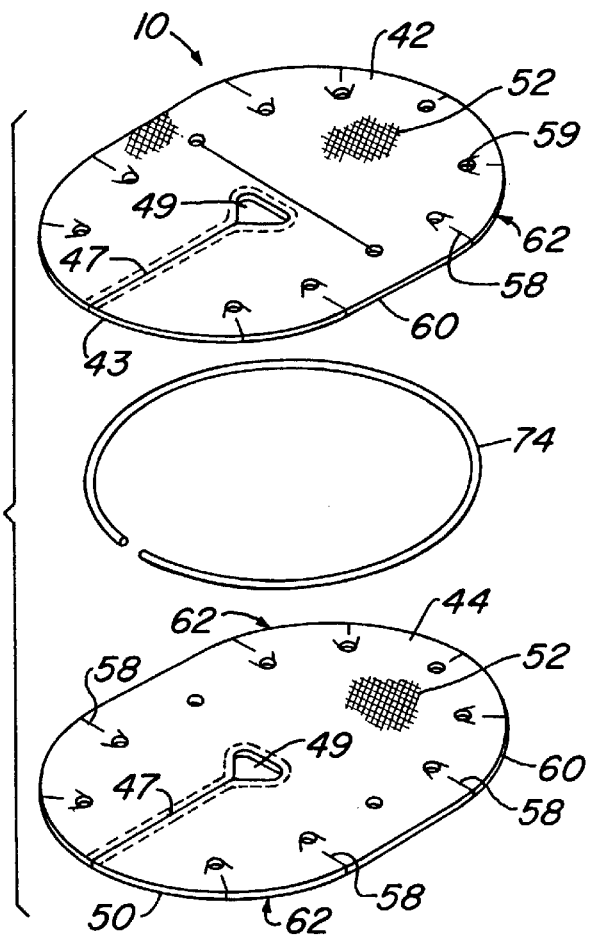
FIG. 3 is an exploded view of the surgically implantable hernia repair mesh patch shown in FIG. 2 that shows the two layers of the mesh.

Hernia mesh patch 10 is illustrated in FIGS. 2 and 3. Hernia mesh patch 10 is designed for a Lichtenstein repair of an inguinal hernia 14. Hernia mesh patch 10 is composed of two similarly sized and shaped pieces or a top layer 42 and a bottom layer 44. Top layer 42 and bottom layer 44 are made of an inert synthetic mesh material, which is preferably a polypropylene material. The mesh material is formed from monofilament material that is resistant to infection and that has been used safely in many hernia operations in previous ways and in previous embodiments. Preferably, top layer 42 and bottom layer 44 of mesh material are made in respective circle, loop, ovoid, or oval shapes. In the embodiment, patch 10 is oval, having two curved ends 43 and two straight sides 45. The bottom layer 44 may be the same size as the top layer 42, as shown, or differ slightly.

A slit 47 (FIGS. 2 and 3) is formed in top layer 42 and bottom layer 44, extending inward from an edge and terminating in an enlarged opening 49. In this embodiment, slit 47 extends inward from one of the curved ends 43 and is generally normal to curved end 43. Slit 47 is located on a longitudinal or major axis of the oval-shaped patch 10. Opening 49 is short of, but closely spaced to, the minor axis, which bisects patch 10 from straight side 45 to straight side 45. Layers 42, 44, are preferably secured to each other by ultrasonic welding around a seam 46. Seam 46 is located inward from the periphery of layers 42, 44. Additionally, seam 46 is located around slit 47 and interior opening 49. The edges of slit 47 are closely spaced to each other and substantially touch each other.

In one embodiment, seam 46 is located approximately one centimeter in from outer edge 50 of layers 42, 44. Seam 46 has an inner seam 46a and an outer seam 46b. The outer one centimeter of mesh material of layers 42, 44 is left free to serve as a border or apron 51 to fill uneven voids and conform more closely to the patient's body space. Also inside of the seam 46b, a monofilament fiber or spring 74, discussed below, like size holes 59 may be cut in the top and bottom mesh layers 42, 44 and are aligned one above the other. The presence of the holes 59 helps initially to frictionally keep the hernia mesh patch 10 in place. Additionally, v-shaped slits 61 may be cut in the top layer 42 to further help to frictionally keep the hernia mesh patch 10 in place. Thereafter, the patient's scar tissue grows in and around holes 59 and v-shaped slits 61 as well as the mesh material itself to continue to keep the hernia mesh patch 10 in position. Border 51 may also be cut radially or diagonally to create slits 58. Slits 58 create scalloped or fringed edges 60, which form tab portions 62. Tab portions 62 are preferably formed on both the outer one centimeter of mesh materials 52 on the top and bottom of mesh layers 42, 44.

Either bottom layer 44 or top layer piece 42 may be cut to form a slit access opening 66 transversely at the center of patch 10, perpendicular to sides 45 and on the minor axis. Slit 66 creates a finger access into the interior space or pouch 70 formed between the top and bottom layers 42, 44 of the synthetic mesh material. Slit 66 is perpendicular to slit 47. Through the slit 66, a continuous, inert, implantable, monofilament fiber or spring 74 is squeezed temporarily to narrow and to elongate spring 74. Spring 74 is then inserted into the interior space or pouch 70. An opening 71 in spring 74 is positioned to line up with slit 47 (FIG. 2). Ends 74 terminate on opposite sides of slit 47. The spring 74 is then released, and allowed to expand to maintain hernia mesh patch 10 in a planar configuration while spring 74 is compressibly held in the pouch 70 of the hernia mesh patch 10. Spring 74 thereby keeps patch 10 fully extended in a planar arrangement, as shown in FIG. 2. The spring 74 is made of a synthetic material, such as nylon, polypropylene, or polyester. In each embodiment, monofilament spring 74 has a circumference that is slightly larger than the circumference of the pouch 70, which is formed between the top and bottom layers 42, 44 of the synthetic mesh material 46. Spring 74 is held in place by inner seam 46a and outer seam 46b.

Figure 5:
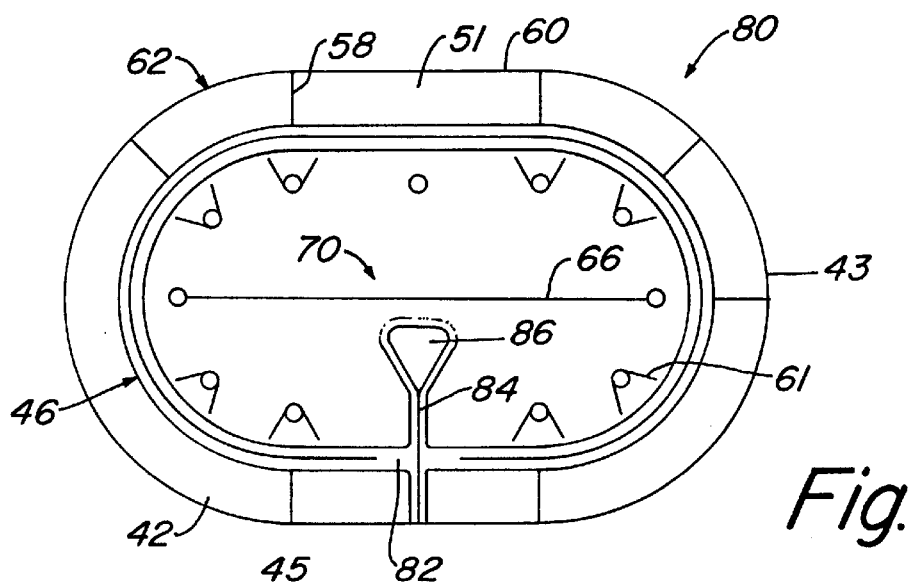
FIG. 5 is a top view of an alternate embodiment of the surgically implantable hernia repair mesh patch.

An alternate embodiment is hernia mesh patch 80, illustrated in FIG. 5. Numbering for similar components of hernia mesh patches 10 and 80 are retained from hernia mesh patch 10 with respect to hernia mesh patch 80. In this embodiment, slit 84 extends inward from one of the straight sides 45 of the hernia mesh patch 80 rather than on curved end 43 of the hernia mesh patch 80. Slit 84 is located on the minor axis and is formed in both top layer 42 and bottom layer 44. Slit 84 terminates in an enlarged opening 86. Seam 46 has an opening 82 for slit 84. Access slit 66 is located on the major axis, parallel to straight sides 45. Opening 86 is between seam 46 and access slit 66.

In use, at the conclusion of the surgeon's use of both sharp and blunt instruments to create a space over the hernia defect in the inguinal canal, the surgeon selects a suitable type and suitably sized hernia mesh patch 10 or 80 for use in the repair of a patient's hernia 14. The selected hernia mesh patch 10 or 80 is folded and further compacted, as may be necessary, by the surgeon's fingers, so that the patch 10 or 80 may be conveniently inserted through the incision 16 and down into the patient's inguinal space. The slit 47 or 84 is slipped around a patient's chord structure and the patch 10 or 80 is positioned such that the interior opening 49 or 86 encircles the patient's chord structure, thereby positioning the patch 10. The hernia mesh patch 10 or 80 is then freed and allowed to expand under the force of the spring 74. Thereafter, the surgeon uses his or her finger to continue any further expansion of patch 10 that may be necessary. The surgeon's finger may be inserted through the slit 66 in the top mesh layer 42 to position the hernia mesh patch 10 within the patient's inguinal space. After the withdrawal of the surgeon's finger, the repair surgery is completed by closing the incision with stitches using the remote incision 16, as illustrated in FIG. 1.

The hernia mesh patches of the invention have a simple design and method of insertion. The hernia mesh patches of the invention adequately overlay a hernia defect by a minimum of two centimeters around the circumference of the hernia defect, with sufficient rigidity and with sufficient friction to eliminate or minimize sliding or migration. When the hernia mesh patch is used, the repair of inguinal and other abdominal wall hernias are repaired through a smaller wound or incision, with less tension, less post-operative discomfort, shorter operating time, and at a potential lower cost to the patient. The patient's post-operative discomfort is decreased, and risk of any recurrence is likewise decreased. The slit for receiving a patient's chord structure enables a surgeon to perform a Lichtenstein repair.

While the invention has been shown in several embodiments, it should be apparent that it is not limited to those embodiments but is susceptible to various changes without departing from the scope of the invention.

We claim:

1. A tissue aperture repair patch for implanting within a patient, comprising:

at least one layer of inert synthetic mesh material sized and shaped to extend across and beyond a tissue aperture in a patient;

a curved, elongated, resilient support member carried by the layer for causing the layer to assume a planar configuration, said member to remain implanted with the layer in the patient;

the layer of inert synthetic mesh material having a periphery extending beyond the support member, defining a border which has a free outer edge to fill uneven voids in a patient's tissue; and a slit in said layer of inert synthetic mesh material, extending inward from the outer edge and terminating in an enlarged opening for placement around a patient's chord structure.

2. The patch according to claim 1 wherein the support member is a monofilament fiber loop and wherein the slit extends inward past the loop, the loop having ends located on opposite sides of the slit.

3. The patch according to claim 1, further comprising:

a second layer joined to the first layer by a seam; and wherein the slit extends inward from the seam through both layers.

4. A tissue aperture repair patch for implanting in a patient, comprising:

a first layer of inert synthetic mesh material sized and shaped to extend across and beyond a tissue aperture in a patient;

a second layer of inert synthetic mesh material secured to the first layer to create a pouch between the first and second layers;

a curved, elongated, resilient support member adjacent a periphery of the pouch for urging both of the layers into a generally flat configuration, the support member being carried within the pouch so as to remain implanted with the layers in the patient; and a slit in said layers of inert synthetic mesh material extending inward from an outer edge of said layers and terminating in an enlarged opening for placement around a patient's chord structure.

5. The patch according to claim 4, further comprising:

an access opening in the pouch for insertion of a finger into the pouch to position the patch across the tissue aperture.

6. The patch according to claim 4 wherein:

the support member is a monofilament fiber.

7. The patch according to claim 4, wherein:

the patch is oval shaped having two curved ends and two straight sides; and wherein the slit extends from one of the curved ends.

8. The patch according to claim 4, wherein:

the patch is oval shaped having two curved ends and two straight sides; and wherein the slit extends from one of the straight sides.

9. A tissue aperture repair patch, comprising:

a first layer of inert synthetic mesh material sized and shaped to extend across and beyond a tissue aperture;

a second layer of inert synthetic mesh material overlying the first layer to create a generally planar configuration for the patch;

the first and second layers being joined together by a seam which defines a pouch between the layers;

a monofilament fiber located within the pouch and adjacent to the seam for urging the patch to conform to the generally planar configuration across the tissue aperture as the surgeon withdraws his or her finger;

a slit in said layers extending inward from an outer edge of said layers and terminating in an enlarged opening for placement around a patient's chord structure; and an access opening in the pouch for providing entry into an interior of the pouch to position the patch across the tissue aperture.

10. The patch according to claim 9, wherein:

the patch is oval shaped having two curved ends and two straight sides; and wherein the slit extends from one of the curved ends.

11. The patch according to claim 9, wherein:

the patch is oval shaped having two curved ends and two straight sides; and wherein the slit extends from one of the straight sides.

12. The patch according to claim 9, wherein:

the monofilament fiber has two ends that terminate on opposite sides of the slit.

* * * * *